United States Patent [19]
Tahbaz

[11] 3,946,597
[45] Mar. 30, 1976

[54] FLAW PENETRANT TEST PANEL

[75] Inventor: John A. Tahbaz, Long Beach, Calif.

[73] Assignee: Purex Corporation, Lakewood, Calif.

[22] Filed: Apr. 26, 1974

[21] Appl. No.: 464,348

[52] U.S. Cl. .................................. 73/53; 73/104
[51] Int. Cl.² ................... G01N 11/00; G01N 19/08
[58] Field of Search .............................. 73/53, 104

[56] References Cited
UNITED STATES PATENTS
| | | | |
|---|---|---|---|
| 3,164,006 | 1/1965 | Alburger | 73/53 |
| 3,791,198 | 2/1974 | Alburger | 73/53 |

Primary Examiner—Richard C. Queisser
Assistant Examiner—John P. Beauchamp
Attorney, Agent, or Firm—White and Haefliger

[57] ABSTRACT

A flaw penetrant test panel having a sheet metal surface in which are impressed tiny or microscopic flaw simulating cavities distributed over the test surface to receive one or more penetrants being tested, the mouth size of the cavities being in the range of about 1 to 10 thousandth inch and being formed by heating the metal to incipient softening temperature followed by penetration of the surface test area using a needle-like tool proportioned to the desired cavity size and depth and which upon penetration of the metal displaces it in a crater-like rim about the cavity being formed.

9 Claims, 3 Drawing Figures

FLAW PENETRANT TEST PANEL

BACKGROUND OF THE INVENTION

Various metallic products and parts in the forms of castings, forgings, machine components and the like of ferrous as well as non-ferrous compositions are tested for flaws, voids and similar defects which weaken the metal so as potentially to cause failure in its use. A customary practice is to apply to the metal a liquid penetrant which enters the defect and thus enables visual identification of its character including dimension, extent and location. Commonly used today are penetrants composed of fluorescent dyes which become more plainly visible when exposed to ultraviolet light.

SUMMARY OF THE INVENTION

The invention has for its general object to provide an improved panel capable of simple and easy use for the testing of a single penetrant or comparative use in the testing of two or more penetrants to determine the choice to be made between them. Generally contemplated is a rigidized test panel in which is formed tiny cavities of uniform microscopic size which simulate the flaws that may be present in work pieces and which are receptive of the penetrant or penetrants by coating the panel with the penetrant.

The invention contemplates the use of any metal to constitute the test medium and which is sufficiently hard to be resistent to having its surface inadvertently scarred or scratched and which will be productive of the later described cratering of cavities impressed in its surface following heating. Illustrative metals are copper, brass, tin and their alloys, also softer steels, all capable of surface incipient softening by heating and to extents suitable for the cavity formation. A preferred and readily available metal having these qualities is commercial sheet aluminum which in itself is flexibly thin but in use is rigidized by bonding to a relatively thick lamination or core.

A further object of the invention relates to the method used for formation of the cavities which generally employs the steps of first heating the metal to an incipient softening temperature and then penetrating its surface with a needle-like tool dimensioned in accordance with the cavity to be formed so that penetration of the softened metal raises a crater-like rim about the cavity.

In its penetrant testing capacity the invention presents the unique advantage of permitting exact uniformity in the sizes and shapes of the simulated flaws, i.e. the impressed cavities. This feature assures exactness in penetrant tests or comparison conditions in that whether within different areas of a single test panel or within different panels used for comparative purposes the cavities may be uniformly identical.

The features and objects referred to in the foregoing as well as the details of an illustrative embodiment of the invention will be understood more fully from the following description of the accomanying drawing.

DESCRIPTION OF THE PREFERRED EMBODIMENT AND METHOD

The preferred test panel forming material is a rigid laminar composite of aluminum and aluminum alloys, generally indicated at 10, that may be selected from the compositions tabulated in the Alcoa Aluminum Handbook, Copyright 1967 by the Aluminum Company of America, in which reference may be made to pages 46 to 54. For purposes of the invention the aluminum alloy composites are not critical because both as to supporting and surface laminations the relation significant to the invention is primarily physical. Thus the laminar composite may consist of a relatively thicker supporting or core aluminum alloy lamination 11 one or both surfaces of which have claddings 12 of commercial sheet aluminum. The laminar composite 10 is formed by advancing the core 11 and surface cladding or claddings 12 between rollers exerting such high pressure against the laminations as to pressure-bond them together to form an integrated composite. In the following it will be assumed that the alloy core is clad on both sides with thinner sheet aluminum.

Figure 1:
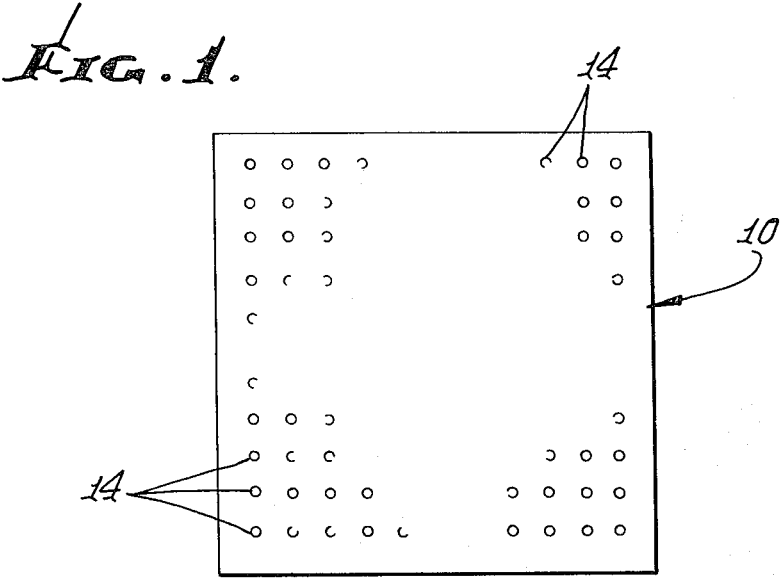
FIG. 1 is a view showing an illustrative test panel surface presented by a sheet aluminum cladding containing distributed spaced cavities shown at enlarged scale.
Figure 2:
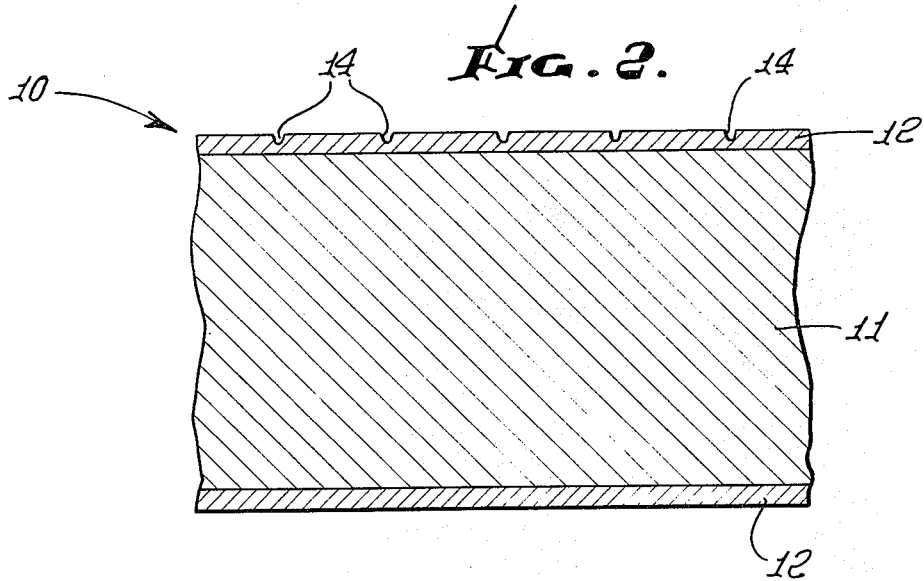
FIG. 2 is an enlarged fragmentary cross section of FIG. 1 showing claddings, one of which is cavitated, bonded to an intermediate or core lamination.
Figure 3:
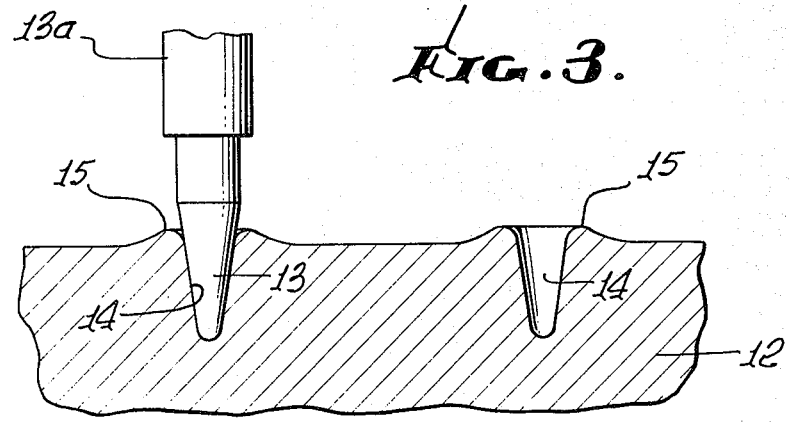
FIG. 3 is a further fragmentary sectional enlargement of the cavitated cladding illustrative of the cavity forming tool and the shapes characteristic of the resulting cavity.

In reference to the drawing, the test panel generally indicated at 10 is shown to consist of a laminar composite core 11 bonded to claddings 12 one only of which need be cavitated as in FIG. 1. As previously observed the relatively thick core 11 serves a supporting and rigidizing function in relation to the thinner cavitated lamination 12.

Typically, the total lamination thickness used to form the test panel is about 0.125 inch with the cladding 12 thicknesses each about 0.003 inch.

As illustrative of the core 11 composition a usable aluminum alloy may contain by weight percentages 0.50 silicon, 0.7 iron, 1.2 to 2.0 copper, 0.3 manganese, 2.1 to 2.9 magnesium, 0.18 to 0.40 chromium, 5.1 to 6.1 zinc, 0.20 titanium, the remainder being aluminum.

A typical cavity-containing commercial aluminum sheet composition applied to at least one surface of the core may be in weight percentages about 0.7 silicon plus iron, 0.10 copper, 0.10 manganese, 0.10 magnesium, 0.8 to 1.3 zinc and the remainder aluminum.

Preparatory to the cavity formation in a rigidized lamination thus typically constituted the aluminum test surface of the panel is first flame or electrically heated to a temperature sufficiently high, and usually in the range of 200°–900°F, to produce incipient softening of the metal preferably to about the penetration depth. The aluminum surface then is immediately penetrated by a suitable needlelike tool which may be a titanium tip 13 carried by a pressure spindle 13a which forces the tip into the metal to a depth that may be from about 1 to 20 thousandth inch or which may roughly correspond to twice the cavity mouth diameter. Suitable stop means, not shown, may limit down travel of the spindle to produce uniform penetrating depth of the tip 13.

Because of difficulties of machining a penetrating tip to its needle-like dimensions the tip may be reduced from machinable proportions to use size by chemical milling, e.g. using known procedures, see U.S. Pat. Nos.

2,965,521; 3,007,780; 3,061,494; 3,082,137; 3,108,919; and 3,745,079. The penetrating tool tip will be reduced to produce a cavity 14 of the stated dimensions having sides tapering inwardly of the panel metal to a somewhat rounded bottom.

By reason of the preheated state of the metal its penetration by the tool tip raises a simulated crater 15 about the mouth or rim of the cavity which is an aid to visual location of the cavity. As previously observed, the cavities 14 are distributed over a selected test area of the panel at spacings and in patterns selectable by choice with no limitations as to distribution patterns. Thus the cavities may be spaced apart in rows or given other pattern distribution. Preferably the cavity distribution density will range between about 3 to 100 per square inch of the panel test area the total size of which may depend upon specific purposes for which the test is conducted. Where different penetrants are to be compared the cavitated test area may be enlarged to permit visual comparison between different penetrants. Typically panel test area sizes may range from 1 to 20 sq. in.

In use the panel may be coated with any of the customarily used dye or penetrant solutions, or different dye solutions where a comparitive test is being made, so that the dyes enter the cavities and after removal of surface excesses color the panel surface in accordance with the penetrant coloration which, as previously mentioned, may be determined by inspection using ultra-violet light in the case of the fluoresecent penetrants.

I claim:

1. A flaw penetrant test panel having a sheet metal surface in which are formed tiny flaw simulating cavities distributed over said surface to receive test penetrant, the mouth size of the cavities being in the range of about 1 to 10 thousandth inch, the cavities being formed by heating the surface layer of the sheet metal to incipient softening and forcing a penetrating tool into the surface layer to a desired depth whereby cavities having crater-like raised rims are formed.

2. Panel according to claim 1 in which the cavity depth is about 1 to 20 thousandth inch.

3. Panel according to claim 1 in which the surface area distribution of the cavities is about 3 to 100 per square inch.

4. Panel according to claim 1 in which said panel is a surface lamination rigidized by bonding to a supporting metallic lamination.

5. Panel according to claim 4 in which said surface lamination is commercial grade sheet aluminum.

6. Panel according to claim 5 in which said supporting lamination is sheet aluminum alloy.

7. A flaw penetrant test panel having a sheet metal surface in which are formed tiny flaw simulating cavities distributed over said surface to receive test penetrant, the mouth size of the cavities being in the range of about 1 to 10 thousandth inch, said cavities having crater-like raised rims.

8. Panel according to claim 7 in which the cavity depth is about 1 to 20 thousandth inch.

9. Panel according to claim 7 in which said panel is a surface lamination of commercial grade sheet aluminum rigidized by bonding to a supporting metallic lamination.

* * * * *